United States Patent [19]
Guiney

[11] 4,041,945
[45] Aug. 16, 1977

[54] MIXING SYRINGE

[76] Inventor: Aeneas C. Guiney, 2855 Silverhill, Pontiac, Mich. 48055

[21] Appl. No.: 693,423

[22] Filed: June 7, 1976

[51] Int. Cl.² .......................................... A61M 5/00
[52] U.S. Cl. ............................ 128/218 M; 128/272.1
[58] Field of Search ....... 128/218 M, 218 R, 218 NV, 128/272, 272.1, 220, 215, 216

[56] References Cited
U.S. PATENT DOCUMENTS

| | | | |
|---|---|---|---|
| 2,305,278 | 12/1942 | Smith | 128/218 M |
| 2,313,483 | 3/1943 | Smith | 128/218 M |
| 2,590,900 | 4/1952 | Sommerstein | 128/218 M |
| 2,869,543 | 1/1959 | Ratcliff et al. | 128/218 M |
| 3,380,451 | 4/1968 | Porter et al. | 128/218 M |
| 3,477,432 | 11/1969 | Shaw | 128/218 M |
| 3,779,371 | 12/1973 | Rovinski | 128/272.1 X |
| 3,838,689 | 10/1974 | Cohen | 128/218 M |

Primary Examiner—John D. Yasko
Attorney, Agent, or Firm—Fisher, Gerhardt & Groh

[57] ABSTRACT

A single barrel mixing syringe in which one material such as a liquid is stored in the bore of the syringe barrel and another material such as a powder is stored in a chamber formed in a resilient piston head which forms not only the powder containing compartment but also the seals preventing leakage of liquid from the syringe. The two chambers are separated by a wall which may be displaced in one embodiment by differential pressure during movement of the piston portion of the syringe and in another embodiment by a separate plunger which displaces the wall.

6 Claims, 5 Drawing Figures

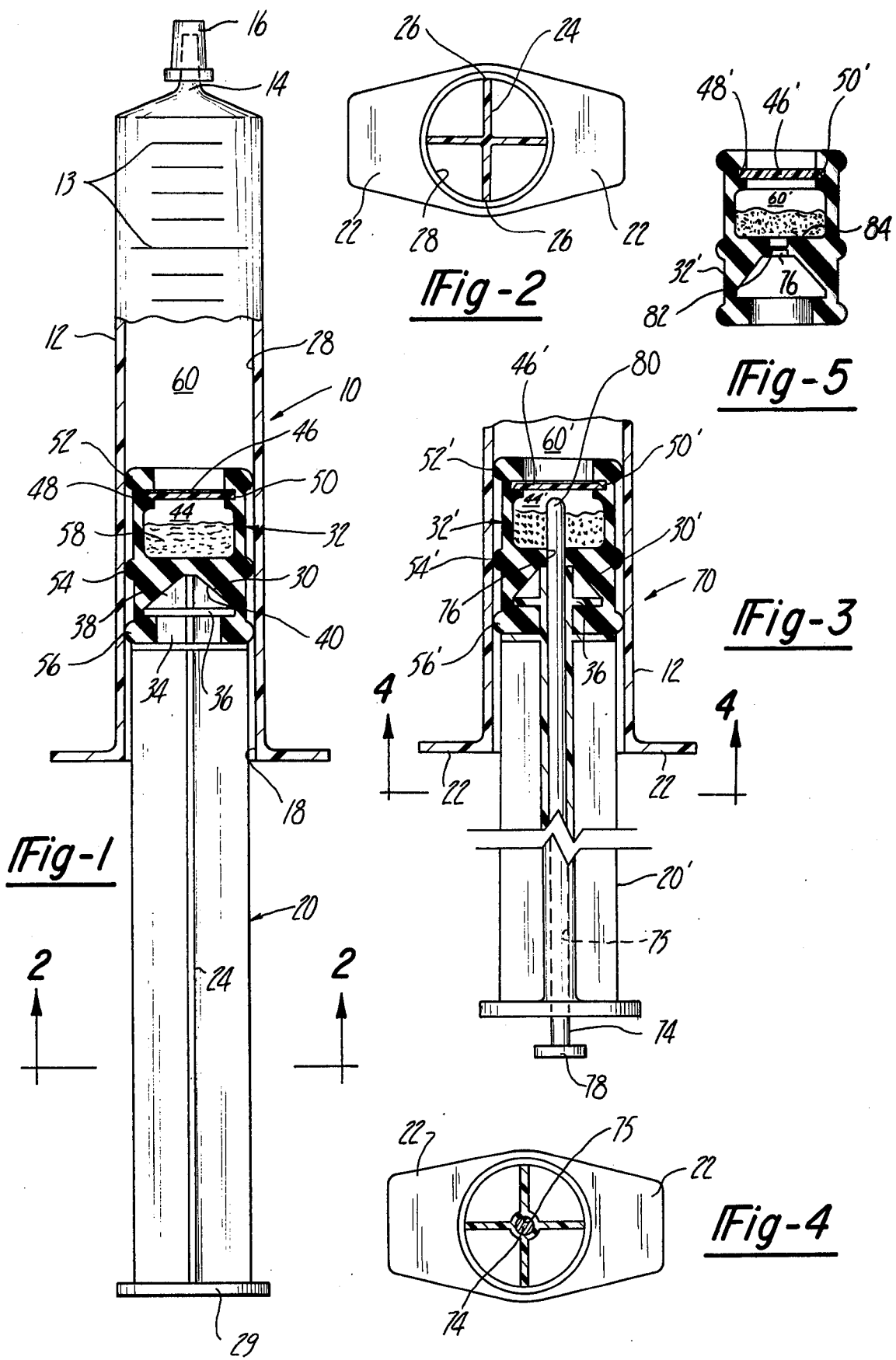

MIXING SYRINGE

This invention relates to hypodermic syringes in which two materials are stored separately within the syringe until shortly before they are mixed together and ejected from the syringe.

Syringes for storing and mixing materials such as a powdered pharmaceutical or medication in one compartment and a diluent or solvent in another compartment are known. Prior to use, the diluent or solvent and the powdered material are mixed together internally of the syringe so that they may be ejected through a hypodermic needle or opening in the syringe.

Syringes of this type have taken many forms and have included syringes with telescoping barrels, plugs, frangible diaphragms and the like. For the most part many of these devices become very complex and are difficult to use without contaminating the materials being mixed.

It is an object of the invention to provide a single barrel hypodermic syringe in which materials may be stored separately for mixing together just prior to use.

Another object of the invention is to provide a syringe in which one of the materials may be premeasured and stored for insertion into a syringe at the time of use.

Still another object of the invention is to provide a single cylinder syringe in which accurately measured amounts of powdered material and liquid solvent can be stored completely separately from each other and which can be mixed without contamination just prior to use.

Still another object of the invention is to provide a mixing syringe of this type in which the entire operation may be carried out with one hand.

A syringe for storing two materials in separate chambers until shortly before the materials are mixed together for ejection from the syringe has been provided in which one chamber is formed within the barrel of the syringe itself and in which the other chamber for storing the other material is formed in a resilient piston head. The resilient piston head forms sealing portions to prevent liquid leakage and supports a movable wall which maintains the two materials separate. When the materials are to be mixed the wall is displaced in one embodiment of the invention by pressure differential acting on a wall during movement of the syringe plunger in the cylinder of the syringe. In another embodiment of the invention the wall separating the two materials is displaced by an auxiliary plunger. The two materials to be mixed and dispensed are maintained separately until just prior to use and if desired one of the materials stored in the chamber formed in the piston head may be stored separately from the remainder of the syringe until just prior to use.

FIG. 1 is a sectional view of the mixing syringe embodying the invention;

FIG. 2 is a cross-sectional view taken on line 2—2 in FIG. 1;

FIG. 3 is a sectional view of another embodiment of the invention;

FIG. 4 is a cross-sectional view taken generally on line 4—4 in FIG. 3; and

FIG. 5 is a view of the piston head portion of the syringe before assembly in the syringe.

Referring to the drawings and particularly to FIG. 1, the mixing syringe embodying the invention is designated generally at 10. The syringe 10 includes a cylinder or barrel 12 which may be formed of glass but most practically can be formed from a transparent plastic material which not only is strong but also is inert to nearly all types of medication. The transparent cylinder is provided with indicia or graduations such as those designated at 13 for indicating the volume of liquid in the cylinder 12.

The cylinder 12 has a nipple or needle adapter 14 formed at one end which is adapted to fit a standard hypodermic needle. The needle adapter 14 is fitted with a protective cap 16 which may remain in place during storage of the syringe and which is removed at the time that the syringe is fitted with a hypodermic needle or other fitting, not shown, for conveying the liquid mixture from the mixing syringe 10.

One end of the cylinder 12 is open as indicated at 18 to slidably receive the plunger assembly 20. Adjacent the open end 18 of the tube 12, provision is made for radially outwardly extending and diametrically opposed flange portions 22 which serve as handles engaging the fingers of the user during operation of the syringe.

The plunger 20 is preferably made of a plastic material and includes longitudinally extending web portions 24 generally coextensive in length to the length of the cylinder 12. The longitudinal web portions 24 has a cross section in the form of a cross, as best seen in FIG. 2, so that the longitudinal extending edges slidably engage the internal walls of bore 28 to guide the plunger during its movement in the barrel 12. The exposed end of the plunger is provided with a thumb rest or pad 29.

The interior end of the plunger 20 is formed with a attaching member 30 which is adapted to support a piston head member 32. The attaching member 30 includes a stem portion 34, a flange 36 and a pilot portion 38 all of which are formed integrally to each other at one end of the plunger assembly 20.

Thus far the syringe 10 which has been described is generally conventional except for the piston head portion 32 and is of a type commonly used in the medical field. Such syringes are considered to be disposable and are typically discarded after a single use although they are sufficiently durable to be employed more than one time.

The piston head assembly 32 is made of an elastomeric, rubber like material. As seen in FIG. 1, the lower end of the piston head member 32 is provided with a cavity 40, the walls of which conform generally to the shape of the attaching portion 30 at the end of the plunger 20. The piston head member 32 deflects sufficiently so that the attaching portion 30 may be inserted in the cavity 40 and when the attached piston head 32 is disposed in the bore 28 of the cylinder 12, radial distortion of the cylinder head 32 is restricted and the attaching portion 30 is retained securely in the cavity 40.

The upper portion of the piston head member 32 as seen in the drawings is provided with a chamber or compartment 44. The chamber 44 is closed from the internal bore 28 of the cylinder 12 by a wall element 46 which preferably is made of a relatively rigid material. The wall member 46 is held in position in an internal annular groove 48 formed in the piston head member 32 at one side of the cavity 44. The peripheral edges of the movable wall 36 are beveled as indicated at 50 to act as a cam or guide to deflect the edges of the groove 48 and permit relatively easy axial displacement of the wall element 46 relative to the piston head member 32.

The outer portion of the piston head member 32 is formed with annular seal portions 52, 54 and 56 which are adapted to engage the interior wall 28 of the cylinder 12 and act as seals preventing fluid passage from within the bore 28 and around the piston head member 32.

The compartment 44 is intended to be partially filled with an accurately measured amount of powdered material indicated at 58 and when the piston head 32 is in one end of the barrel 12, the bore 28 forms another chamber 60 in which a liquid solvent for the powdered material is introduced in a carefully measured quantity and stored until the time for mixing with powder 58.

Sterility against contaminants is very important in hypodermically injected medications and as a consequence the present mixing syringe is assemblied under such sterile conditions. The cavity 44 in the piston head 32 is loaded with a carefully measured amount of powdered material after which the wall 46 is inserted to close the chamber 44 and the plunger assembly 20 together with the piston head 32 is inserted into the cylinder 12. Thereafter liquid solvent or solution may be loaded through the opening in the needle adapter 14 to the chamber 60 after which the cap 16 may be placed in position. The mixing syringe 10 may then be stored until it is used.

To use the mixing syringe 10 it simply is necessary to depress the plunger 20 by placing the cylinder 12 between two of the fingers of one hand and press on the plunger thumb rest 29. Since the cavity 44 is not completely filled with powder, movement of the piston head 32 into the cylinder bore 28 causes an increase in pressure in the chamber 60 formed in the barrel 12 and the pressure differential acting on the wall 46 causes it to be displaced into the chamber 44. Upon displacement of the wall 46 the powder and liquid is free to mix. After the complete mixing of the two materials within the mixing syringe, the cap 16 may be removed and replaced with a hypodermic needle or tube for injection or dispensing.

Referring now to FIGS. 3 and 4 illustrating another embodiment of the invention, the syringe is designated at 70 and includes the cylinder barrel 12 which is identical to that shown in FIGS. 1 and 2 embodiment. However, the plunger assembly 20' differs from the plunger assembly 20 in that a push rod 74 is supported for sliding movement longitudinally of the plunger 20' in an axially extending bore 75. The rod 74 is longer than the plunger assembly 20' and extends from its opposite ends. The rod 74 projects through the attaching member 30' through an opening 76 in the piston head member. The piston head member 32' has a wall element 46' seated in an annular groove 48'. In this instance the beveled portion 50' faces in the opposite direction from surface 50 shown in FIG. 1. The rod 74 is provided with a finger pad 78 for moving the rod 74 axially in bore 75 and relative to the remainder of the plunger assembly 20'. When the rod 74 is so moved, the inner end 80 engages the wall 46' and displaces it and separates it from the piston head member 32' so that the chamber 44' is open to the chamber 60' formed in the barrel 12. The cam surfaces 50' facilitate dislodging wall 46' from the groove 48'.

Referring to FIG. 5 the piston head member 32' is shown prior to its assembly into the syringe 10'. The opening 76 is provided with a membrane or diaphragm 82 of thin material which is molded with the remainder of the piston head member 32' and serves to retain powdered material in the chamber 44.

To assemble the syringe shown in FIGS. 3 and 4, the head member 32' is attached to the attachment portion 30' on the plunger 20' and the attached piston head 32' is inserted into the bore 28' of the barrel. Thereafter, the rod 74 may be inserted in the axial bore 75. Just prior to use, the rod 74 is displaced relative to the plunger to pierce the membrane 82 so that the end of the rod enters the chamber 44'. To initiate mixing, the wall is displaced by the end 80 of the rod. After a thorough mixing of the powder and liquid the cap 16 may be removed from the needle adapter 14 and the latter may be connected to a hypodermic needle or hose. Thereafter, the plunger 20' as well as the rod 74 are moved simultaneously in the barrel so that the liquid mixture may be displaced from the syringe. During such displacement the liquid is prevented from leaking around the rod 74 by the resilient piston head member 32 and particularly a flange portion 84 around the opening 82 which is smaller than the diameter of the rod 74. As a result, the flange 84 forms a seal means engageable in fluid tight relationship with the outer surface of rod 74. The surfaces of piston head member 32 pressing against the flange also act to seal liquid from passing through the opening 75.

The use of the embodiments shown in FIGS. 3 and 4 is substantially the same as that of the embodiment shown in FIG. 1. With the FIG. 3 embodiment, the rod 74 is used to pierce the membrane 82 and subsequently to displace the wall member so that the chambers 44' and 60' communicate with each other for mixing of the powdered material and diluent. After sufficient mixing, the syringe 10 is provided with a hypodermic needle or other fluid connection and the liquid mixture may be displaced from the syringe in the usual manner. In other words, by holding the syringe in one hand with fingers engaged with diametrically opposed flanges 22, the thumb may be placed on the rests 78 and the rod 74 and plunger 20' are moved simultaneously so that the piston head 32' displaces the liquid from the bore 28'.

In both embodiments the attaching portions 30 and 30' of the plunger assemblies 20 and 20' prevent radial inward deflection of the annular seals 54 and 56 or 54' and 56' to insure that the seals remain in engagement with the walls of bore 28 in the cylinder 12. Similarly, the displaceable walls 46 and 46' are seated in their respective grooves 48 and 48' to resist radial inward deflection of the annular seal portions 52 or 52' to insure good sealing contact between the walls of bore 28 and the seal surfaces. Also in both embodiments, the cam surfaces 50 and 50' permit relatively easy displacement of the wall elements 46 and 46'.

A mixing syringe has been provided in which two different materials may be stored and maintained separately from each other until just prior to intended use at which time the two materials may be mixed together. One of the materials is stored in a chamber formed by the syringe barrel and plunger and the other material is stored in a chamber formed in a resilient piston head detachably connected to the plunger. The piston head forms a separate chamber having a movable wall acting to separate the two materials from each other when the syringe is fully assembled. In one embodiment the wall separating the two materials is displaced upon movement of the plunger in the syringe barrel and in another embodiment an auxiliary plunger is provided to mechanically displace the wall between the two chambers.

The embodiments of the invention in which an exclusive property or privilege is claimed are defined as follows:

1. A syringe assembly for storing two materials separately in readiness for mixing together and for injection as a liquid at the time of use, the combination of; a tubular cylinder, a needle adapter formed by one end of said cylinder for communication with the interior of said cylinder and being adapted to receive a hypodermic needle, a plunger slidably disposed in said cylinder and projecting from an open end thereof, said plunger forming a first chamber therein, a movable wall member forming part of said plunger and a wall of said first chamber, a second chamber formed in said cylinder between said plunger and said needle adapter, said second chamber being adapted to contain one of the materials to be mixed and said first chamber containing the other of said materials, said plunger having a head portion forming said first chamber, said movable wall member being relatively rigid and having a peripheral edge portion normally seated in sealing engagement with said head portion to separate said first and second chambers from each other, and means to displace said wall and open said chambers to each other for mixing said materials, said plunger being movable towards said needle adapter to displace said mixed materials from said cylinder.

2. A syringe assembly for storing two materials separately in readiness for mixing together and for injection as a liquid at the time of use, the combination of; a tubular cylinder, a needle adapter formed by one end of said cylinder for communication with the interior of said cylinder and being adapted to receive a hypodermic needle, a plunger slidably disposed in said cylinder and projecting from an open end thereof, said plunger forming a first chamber therein, a movable wall member forming part of said plunger and a wall of said first chamber, a second chamber formed in said cylinder between said plunger and said needle adapter, said second chamber being adapted to contain one of the materials to be mixed and said first chamber containing the other of said materials, and means to displace said wall and open said chambers to each other for mixing said materials, said plunger being movable towards said needle adapter to displace said mixed materials from said cylinder, said plunger having a resilient head portion formed of flexible material and said first chamber being forming in said flexible head portion, and said movable wall member being relatively rigid and having a peripheral edge portion seated in a groove formed by said flexible head portion.

3. A combination of claim 2 in which said flexible head portion forms resilient seals in engagement with the interior walls of said cylinder to prevent fluid passage past said resilient head portion upon movement of said plunger in said cylinder.

4. The combination of claim 2 in which said means for displacing said movable wall includes a member supported in said plunger for movement relative thereto into engagement with said wall means to displace the latter independently of movement of said plunger.

5. The combination of claim 2 in which said plunger includes an attaching member and in which said head portion is detachably supported on said attaching portion.

6. The combination of claim 2 and further comprising a separate member movable relative to said plunger to displace said wall element, and seal means formed by said resilient head portion for preventing fluid passage from said first chamber around said member.

* * * * *